United States Patent [19]

Palmere et al.

[11] Patent Number: 5,047,581

[45] Date of Patent: Sep. 10, 1991

[54] ISOLATION OF CIS-ISOMERS FROM ISOMERIC MIXTURES OF CIS/TRANSCYCLOPROPANECARBOXYLATES

[75] Inventors: Raymond M. Palmere, West Orange; Thomas E. Guralski, Trenton, both of N.J.

[73] Assignee: FMC Corporation, Philadelphia, Pa.

[21] Appl. No.: 398,674

[22] Filed: Aug. 25, 1989

[51] Int. Cl.$^5$ .................... C07C 51/347; C07C 51/42
[52] U.S. Cl. ...................................................... 562/506
[58] Field of Search ........................................ 562/506

[56] References Cited

U.S. PATENT DOCUMENTS

| | | | |
|---|---|---|---|
| 3,637,823 | 1/1972 | Berg et al. | 562/506 |
| 3,903,113 | 9/1975 | Bradshaw et al. | 562/506 |
| 3,943,167 | 3/1976 | Suzukamo et al. | 562/506 |
| 4,228,299 | 10/1980 | Ferguson et al. | 562/506 |
| 4,229,593 | 10/1980 | Kondo et al. | 562/506 |
| 4,236,026 | 11/1980 | Naumann | 562/506 |
| 4,306,077 | 12/1981 | Leigh | 562/506 |
| 4,332,815 | 6/1982 | Engel | 560/124 |
| 4,419,524 | 12/1983 | Lindwurm et al. | 562/506 |
| 4,551,281 | 11/1985 | Crosby | 560/124 |

*Primary Examiner*—J. E. Evans
*Attorney, Agent, or Firm*—Stanford M. Back; H. Robinson Ertelt

[57] ABSTRACT

The treatment of isomeric mixtures of cis/trans -3-(2,2-dihalo-3,3,3-trifluoropropyl)-2,2-dimethylcyclopropanecarboxylic acid esters with excess base at elevated temperatures hydrolyzes the ester, dehydrohalogenates the side chain, and thereafter selectively converts the resulting unsaturated side chain of the corresponding trans-cyclopropanecarboxylic acid to an acetyl byproduct, from which may be readily separated and recovered an enriched concentration of the desired cis-2-halo-1-propenylcyclopropanecarboxylic acid, together with minor amounts of the corresponding transacid.

12 Claims, No Drawings

ISOLATION OF CIS-ISOMERS FROM ISOMERIC MIXTURES OF CIS/TRANSCYCLOPROPANECARBOXYLATES

CROSS-REFERENCE TO RELATED APPLICATION

The subject matter of this application is related to that of U.S. application Ser. No. 323,652, filed Mar. 15, 1989 in the name of John H. Hoare, which describes an improved process for preparation of the esters of a mixture of cis and trans- ("cis/trans")-3-(2-halo-3,3,3-trifluoro-1-propenyl)-2,2-dimethylcyclopropanecarboxylic acid, employing a novel catalyst system.

BACKGROUND OF THE INVENTION

The present invention relates to a process whereby cis isomers of certain preferred cyclopropanecarboxylic acids may be isolated from an isomeric mixture of cis/trans-cyclopropanecarboxylates. More specifically, it relates to the isolation of a product significantly enriched in cis-3-(2-halo-3,3,3-trifluoro-1-propenyl)-2,2-dimethylcyclopropanecarboxylic acid starting with esters of a mixture of cis/trans-3-(2,2-dihalo-3,3,3-trifluoropropyl)-2,2-dimethylcyclopropanecarboxylic acid.

Pyrethroid compounds are known to be useful as insecticides. Amongst these, pyrethroid esters of cis-3-(2-chloro-3,3,3-trifluoro-1-propenyl)-2,2-dimethylcyclopropanecarboxylic acid are more active insecticides than the corresponding esters of the trans isomer of this acid.

However, as demonstrated by U.S. copending application Ser. No. 323,652 (above), which is also directed to the dehydrohalogenation of esters of cis/trans-3(2,2-dihalo-3,3,3-trifluoropropyl)-2,2-dimethylcyclopropanecarboxylic acid to the corresponding 2-halo-1propenyl compound, the ratio of cis:trans isomers does not vary during the course of this dehydrohalogenation reaction.

These products, and particularly the aforesaid cis isomers, are useful, for example, as foliar and soil insecticides against such insects as species of Diabrotica. Therefore, processes which provide predominant amounts of the cis isomer are especially desired.

SUMMARY OF THE INVENTION

In accordance with the present invention, it has been found that the treatment of isomeric mixtures of cis/-trans-3-(2,2-dihalo-3,3,3-trifluoropropyl)-2,2-dimethylcyclopropanecarboxylic acid esters with excess base at elevated temperatures hydrolyzes the ester, dehydrohalogenates the side chain, and thereafter selectively converts the resulting unsaturated side chain of the corresponding trans-cyclopropanecarboxylic acid to an acetyl byproduct, from which may be readily separated and recovered an enriched concentration of the desired cis-2-halo-1-propenylcyclopropanecarboxylic acid together with minor amounts of the corresponding trans-acid, wherein "halo" is fluoro, chloro, or bromo, and preferably chloro. The esters are principally and most desirably lower alkyl esters having from about 1 to 6 carbon atoms.

DETAILED DESCRIPTION OF THE INVENTION

In copending application Ser. No. 323,652 (above) there is described an isomeric mixture of cis/trans-esters of 3-(2,2-dihalo-3,3,3-trifluoropropyl)-2,2-dimethylcyclopropanecarboxylic acid, which may be used as the starting materials of this invention, wherein the weight ratio of the cis:trans isomers in this mixture depends principally upon how they are prepared. Generally, for purposes of this invention, the optimum economic benefits are obtained when these ratios range from about 60:40 to 80:20 of cis:trans. For the preparation of these materials see also U.S. Pat. Nos. 4,332,815 and 4,551,281 (above). It is these materials which, when utilized in the instant process, provide cis/trans-3-(2-halo-3,3,3-trifluoro-1-propenyl)-2,2-dimethylcyclopropanecarboxylic acid having an enhanced cis content of at least about 85 weight %, up to about 96–98%, with the balance comprising the corresponding trans-isomer.

In carrying out the instant process there is required initially at least two moles of base per mole of ester starting material just to hydrolyze the mixture of cis/-trans esters to the corresponding acid and to dehydrohalogenate the 2,2-dihalo-3,3,3-trifluoropropyl side chain to the 2-halo-3,3,3-trifluoro-1-propenyl group. However, in accordance with this process, any additional base in excess of the two moles required for the above reactions selectively reacts with the trans-3-(2-halo-3,3,3-trifluoro-1-propenyl)-2,2-dimethylcyclopropanecarboxylic acid to produce a byproduct, trans-3-acetyl-2,2-dimethylcyclopropanecarboxylic acid. The cis-3-(2-halo-3,3,3-trifluoro-1-propenyl)-2,2-dimethylcyclopropanecarboxylic acid may then be separated and recovered from this byproduct in high concentration by adjusting the pH of the reaction product to about 7.2 to 7.4, by, e.g., acidification, followed by filtration, or by extraction of the cis material with an organic solvent such as methylene chloride or the like from the aqueous reaction product mixture.

Thus, while at least two moles of base are necessary to complete the hydrolysis and dehydrohalogenation, additional amounts are necessary to react with the trans-isomer to form the aforementioned acetyl by-product from which the cis-isomer may then be readily recovered. Therefore, preferably a total of at least about 4 moles of base per mole of isomer starting material are required for the process, and most preferably at least about 4.5 moles of base per mole of the cis/trans mixture. Molar ratios of base below 4 either contribute to incomplete reactions, as in Examples 9–16 and 19–22, or the resulting improvement in the cis/trans ratio is below the optimum, as in Examples 17 and 18. The maximum amount of base is limited only by its solubility in the solvent and the economics of the cost of additional base. Examples 23 and 24 utilize less than 4 moles of base per mole of reactant, but the reactants in these experiments are the already-dehydrohalogenated cis- and trans-3-(2-chloro-3,3,3-trifluoro-1-propenyl)-2,2-dimethylcyclopropanecarboxylic acid. These reactants thus require two fewer moles of base per mole of reactant because neither hydrolysis nor dehydrohalogenation is required.

The bases employed in this process are desirably strong alkali metal bases, of which potassium hydroxide and sodium hydroxide are preferred. Although both are strong bases, a comparison of Examples 6 and 7 (below) shows potassium hydroxide to be the more preferred base because of the higher cis to trans product ratio obtained.

The solvent employed is desirably a mixture of alcohol and water. Of these, a mixture of methanol and water is preferred. The ratio of methanol to water is not critical and may vary from about 1.5 to 10 volumes of methanol per volume of water. However, as shown in the examples, when a high ratio of methanol to water is used, as in Example 18, a long reaction time is generally required, and the product exhibits a relatively small improvement in the cis/trans ratio. On the other hand, a methanol/water ratio of about 1.67:1 to about 2:1 provides a much improved benefit to the cis/trans ratio, provided that an adequate amount of base is present. Therefore, the optimum volume ratio of methanol to water is desirably about 1.6:1 to 2:1, and preferably should not exceed approximately 4:1.

The concentration of cis/trans starting material in the solvent is likewise not critical, and may be as low as about 0.1 g/mL of solvent up to at least about 0.5 g/mL, and preferably about 0.4 g/mL.

The temperature employed may also be varied considerably, but is preferably reflux temperature. One factor affecting the reflux temperature is the ratio of methanol to water; another factor is the concentration of reactants in the solvent. Since the preferred ratio of methanol to water is about 2/1 and the preferred concentration of starting material in the solvent is about 0.4 g/mL, both factors favor a higher reflux temperature and, therefore, more rapid reaction. Under these conditions a reaction time of at least about 12 hours appears adequate, while about ten hours appears to be a minimum time.

The preferred method of isolating the predominantly cis-3-(2-chloro-3,3,3-trifluoro-1-propenyl)-2,2-dimethylcyclopropanecarboxylic acid from trans-3-acetyl-2,2-dimethylcyclopropanecarboxylic acid is to adjust the pH of the reaction mixture to about 7.2 to 7.4, preferably with an acid such as hydrochloric acid, and then extract the cis-material, together with minor amounts of unconverted trans isomer, with a solvent, such as methylene chloride, leaving the trans-acetyl byproduct behind in solution Care must be taken to maintain the pH at about 7.2 to 7.4 during the extraction process and to allow a complete separation of the phases for maximum yield of the desired product. The product can then be recovered from the extract by conventional methods. Alternatively, instead of solvent extraction, the desired product may be recovered from the acidified reaction material by filtration.

The process of this invention will now be illustrated by the following examples, as reported in Table I, of which the conditions and methods of Examples 3 and 6 are typical. In these examples it will be noted that as the mole ratio of base to starting material decreased, the ratio of cis to trans product likewise decreased. Thus, maximum benefits were obtained in Examples 1 to 8, with lesser benefits in the remaining examples.

In the examples, an "incomplete reaction" signifies that not enough base was employed, i.e. less than about 4.5 moles, as described above. Also, methanol/water ratios are by volume; while yield % is based on the weight of the starting material.

Examples 23 and 24 are included to demonstrate the relative reactivities of cis- and trans- cyclopropanecarboxylic acids with excess base. All conditions in the two experiments are identical except for the virtually 100% cis (Example 23); or 100% trans (Example 24) starting material, yet the results are very different. Not only is there a nearly quantitative recovery of material in Example 23, but also there is very little byproduct formed. In contrast, a significantly smaller percentage of starting material is recovered in Example 24, and nearly one-half of that which is recovered is byproduct.

EXAMPLES

Example 3

Reaction of methyl cis/trans 3-(2,2-dichloro-3,3,3-trifluoropropyl)-2,2-dimethylcyclopropanecarboxylate and excess potassium hydroxide and isolation of product at pH 7.4.

To 125 mL of water was added 150 g (2.3 moles) of 86% potassium hydroxide. The resulting solution was diluted with 200 mL of methanol after which 150 g (0.51 mole) of methyl 3-(2,2-dichloro-3,3,3-trifluoropropyl)-2,2-dimethylcyclopropanecarboxylate (cis to trans ratio=77/23 by gas chromatography) was added during two minutes. An additional 50 mL of methanol was added, and the mixture was heated at reflux for twelve hours. The methanol was evaporated from the mixture under reduced pressure, and the residue was diluted with 1650 mL of water. This aqueous solution was extracted with 150 mL and 50 mL portions of methylene chloride. Evaporation of the combined extracts yielded a residue weighing 0.2 g. The pH of the aqueous phase was adjusted to 7.4 by the addition of 49 mL of 37% hydrochloric acid. Extraction with 200 mL and 50 mL portions of methylene chloride followed. The combined extracts were themselves extracted successively with 300 mL and 50 mL portions of a 10% aqueous solution of potassium hydroxide. The combined aqueous extracts were acidified to pH 2 with 37% hydrochloric acid, precipitating the cyclopropanecarboxylic acid. Filtration recovered 57 g of 3-(2-chloro-3,3,3-trifluoro-1-propenyl)-2,2-dimethylcyclopropanecarboxylic acid having a cis/trans ratio of 95/5.

EXAMPLE 6

Reaction of methyl cis/trans 3-(2,2-dichloro-3,3,3-trifluoropropyl)-2,2-dimethylcyclopropanecarboxylate 3,3,3-trifluoropropyl)-2,2-dimethylcyclopropanecarboxylate and excess potassium hydroxide To a flask containing 75 mL of water was added 52.5 g (0.80 mole) of potassium hydroxide (86% assay). To this mixture was added 75 mL of methyl alcohol. A solution of 59 g (0.20 mole) of methyl 3-(2,2-dichloro-3,3,3-trifluoropropyl)-2,2-dimethylcyclopropanecarboxylate (cis to trans ratio=79/21 as measured by nmr) in 50 mL of methyl alcohol was added to the reaction flask. The reaction mixture was heated at reflux (81° C.) for 24 hours. After the solvents had been evaporated under reduced pressure, 150 mL of distilled water was added to dissolve the solid residue. This solution was acidified with −100 mL of 20% hydrochloric acid and was then cooled at 5° C. for one hour. The solid 3-(2-chloro-3,3,3-trifluoro-1-propenyl)-2,2-dimethylcyclopropanecarboxylic acid was collected by filtration, washed twice with 25 mL of water, and dried in a vacuum oven. The cis/trans ratio of this product was determined by nmr to be 96.4/3.6.

Periodically, when samples were removed from the reaction mixture, the following cis/trans weight ratios of 3-(2-chloro-3,3,3-trifluoro-1-propenyl)-2,2-dimethylcyclopropanecarboxylic acid were found:

| Reaction Time | cis/trans ratio |
| --- | --- |
| 2 hours | 82.4/17.6 |
| 6 hours | 88.9/11.1 |
| 12 hours | 94.8/5.2 |
| 18 hours | 95.4/4.6 |

3,3,3-trifluoropropyl)-2,2-dimethylcyclopropanecarboxylic acid esters which comprises contacting said isomeric mixture with an excess of base in a solvent at elevated temperatures, to hydrolyze the ester, dehydrohalogenate the side chain and selectively convert the unsaturated side chain of the trans cyclopropane carboxylic acid to an acetyl byproduct acidifying the resulting product mixture to a pH of about 7.2 to 7.4, and

TABLE 1

| Examples | Reactant g | (A)[a] Moles | Base g | (B)[b] Moles | Moles (B)/ Moles (A) | Solvent Methanol | (ml) Water | g of (A) mL of Solvent |
| --- | --- | --- | --- | --- | --- | --- | --- | --- |
| 1  | 30     | 0.10 | 29.2   | 0.45  | 4.5/1 | 50   | 25    | 0.4  |
| 2  | 150    | 0.51 | 150    | 2.30  | 4.5/1 | 250  | 135.5 | 0.39 |
| 3  | 150    | 0.51 | 150    | 2.30  | 4.5/1 | 250  | 125   | 0.4  |
| 4  | 750    | 2.56 | 750    | 11.52 | 4.5/1 | 1250 | 625   | 0.4  |
| 5  | 880h   | 3.00 | 879    | 13.5  | 4.5/1 | 1467 | 733.5 | 0.4  |
| 6  | 59     | 0.20 | 52.5   | 0.80  | 4/1   | 125  | 75    | 0.3  |
| 7  | 59     | 0.20 | 32.2[e]| 0.81  | 4/1   | 125  | 75    | 0.3  |
| 8  | 118    | 0.40 | 105    | 1.61  | 4/1   | 200  | 100   | 0.39 |
| 9  | 30     | 0.10 | 19.6   | 0.30  | 3/1   | 40   | 20    | 0.5  |
| 10 | 30     | 0.10 | 19.6   | 0.30  | 3/1   | 200  | 100   | 0.1  |
| 11 | 30     | 0.10 | 19.6   | 0.30  | 3/1   | 48   | 12    | 0.5  |
| 12 | 30     | 0.10 | 19.6   | 0.30  | 3/1   | 240  | 60    | 0.1  |
| 13 | 30     | 0.10 | 16.9   | 0.26  | 2.6/1 | 75   | 25    | 0.3  |
| 14 | 30     | 0.10 | 16.9   | 0.26  | 2.6/1 | 75   | 25    | 0.3  |
| 15 | 30     | 0.10 | 16.9   | 0.26  | 2.6/1 | 75   | 25    | 0.3  |
| 16 | 30     | 0.10 | 16.9   | 0.26  | 2.6/1 | 75   | 25    | 0.3  |
| 17 | 118    | 0.40 | 65     | 1.0   | 2.5/1 | 250  | 100   | 0.34 |
| 18 | 118    | 0.40 | 65     | 1.0   | 2.5/1 | 410  | 50    | 0.26 |
| 19 | 30     | 0.10 | 14.3   | 0.22  | 2.2/1 | 40   | 20    | 0.5  |
| 20 | 30     | 0.10 | 14.3   | 0.22  | 2.2/1 | 200  | 100   | 0.1  |
| 21 | 30     | 0.10 | 14.3   | 0.22  | 2.2/1 | 48   | 12    | 0.5  |
| 22 | 30     | 0.10 | 14.3   | 0.22  | 2.2/1 | 240  | 60    | 0.1  |
| 23 | 30[f]  | 0.12 | 16.1   | 0.25  | 2.2/1 | 75   | 25    | 0.12 |
| 24 | 30[g]  | 0.12 | 16.1   | 0.25  | 2.2/1 | 75   | 25    | 0.12 |

| Examples | Methanol/ Water | Reaction Time (hours) | Temperature[i] (°C.) | (C)[c] cis/trans | Comments |
| --- | --- | --- | --- | --- | --- |
| 1  | 2/1    | 12.5 |    | 95/5     | 51.3% yield[j] of (C) |
| 2  | 1.85/1 | 15   | 76 | 95/5     | 44.9% yield of (C) |
| 3  | 2/1    | 12   |    | 95/5     | 45.9% yield of (C) |
| 4  | 2/1    | 27.5 |    | 95/5     | 44.7% yield of (C) |
| 5  | 2/1    | 12   |    | 94/6     | 38.4% yield of (C) |
| 6  | 1.67/1 | 24   | 81 | 96/4[d]  |  |
| 7  | 1.67/1 | 24   | 81 | 91/9[d]  |  |
| 8  | 2/1    | 34   | 78 | 96/4     |  |
| 9  | 2/1    | 14   |    | 93/7     | Incomplete reaction |
| 10 | 2/1    | 7    |    | 81/19    | Incomplete reaction |
| 11 | 4/1    | 7    |    | 94/6     | Incomplete reaction |
| 12 | 4/1    | 14   |    | 79/21    | Incomplete reaction |
| 13 | 3/1    | 10.5 |    | 83/17    | Incomplete reaction |
| 14 | 3/1    | 10.5 |    | 74/26    | Incomplete reaction |
| 15 | 3/1    | 10.5 |    | 74/26    | Incomplete reaction |
| 16 | 3/1    | 10.5 |    | 71/29    | Incomplete reaction |
| 17 | 2.5/1  | 30   | 78 | 85/15[d] |  |
| 18 | 8.2/1  | 67   | 72 | 83/17[d] |  |
| 19 | 2/1    | 7    |    | 75/25    | Incomplete reaction |
| 20 | 2/1    | 14   |    | 77/23    | Incomplete reaction |
| 21 | 4/1    | 14   |    | 85/15    | Incomplete reaction |
| 22 | 4/1    | 7    |    | 83/17    | Incomplete reaction |
| 23 | 3/1    | 12   |    |          | 4% byproduct;[j] 98% recovery |
| 24 | 3/1    | 12   |    |          | 45% byproduct;[j] 88.3% recovery |

[a]Methyl 3-(2,2-dichloro-3,3,3-trifluoropropyl)-2,2-dimethylcyclopropanecarboxylate
[b]Potassium hydroxide (86% assay)
[c]cis- and trans-3-(2-Chloro-3,3,3-trifluoro-1-propenyl)-2,2-dimethylcyclopropanecarboxylic acid (wt. ratio)
[d]Determined by nmr
[e]Sodium hydroxide
[f]cis-3-(2-Chloro-3,3,3-trifluoro-1-propenyl)-2,2-dimethylcyclopropanecarboxylic acid (cis/trans = 98/2)
[g]trans-3-(2-Chloro-3,3,3-trifluoro-1-propenyl)-2,2-dimethylcyclopropanecarboxylic acid (cis/trans = 0/100)
[h]Undistilled methyl 3-(2,2-dichloro-3,3,3-trifluoropropyl)-2,2-dimethylcyclopropanecarboxylate
[i]Where no temperature is reported - not available
[j]Balance is unreacted starting material

I claim:

1. A process for preparing a product substantially enriched in the cia isomers of 3-(2-halo-3,3,3-trifluoro-1-propenyl)-2,2-dimethylcyclopropanecarboxylic acid from isomeric mixtures of cis- and trans-3-(2,2-dihalo- recovering cis-3-(2-halo-3,3,3-trifluoro-1-propenyl)-2,2-dimethylpropanecarboxylic acid, wherein halo is chloro or bromo.

2. The process of claim 1 wherein at least four moles of base are present for each mole of ester starting material.

3. The process of claim 1 or 2 wherein the base is a strong alkali metal base.

4. The process of claim 1 wherein the said product mixture is adjusted with acid to a pH of about 7.2 to 7.4, followed by extraction of the cis-3-(2-halo-3,3,3-trifluoro-1-propenyl)-2,2-dimethylcyclopropanecarboxylic acid from the product mixture with a solvent.

5. The process of claim 1 wherein the said product mixture is adjusted with acid to a pH of about 7.2 to 7.4, followed by filtration and recovery of the cis-3-(2-halo-3,3,3-trifluoro-1-propenyl)-2,2-dimethylcyclopropanecarboxylic acid from the product mixture.

6. The process of claim 1 or 5 wherein the solvent is a mixture of methanol and water.

7. The process of claim 6 wherein the volume ratio of methanol to water is from about 1.5:1 to 10:1.

8. The process of claim 6 wherein the volume ratio of methanol to water is from about 1.6:1 to 4:1.

9. The process of claim 1 wherein the temperature is reflux temperature.

10. A process for preparing cis isomers of 3-(2-chloro-3,3,3-trifluoro-1-propenyl)-2,2-dimethylcyclopropanecarboxylic acid in high concentration by weight from isomeric mixtures of cis- and trans-3-(2,2,-dichloro-3,3,3-trifluoropropyl)-2,2-dimethylcyclopropanecarboxylic acid esters which comprises contacting said isomeric mixture with at least four moles of base for each mole of ester staring material in a solvent at elevated temperature, acidifying the resulting product mixture with about 0.7 moles of hydrochloric acid per mole of base and recovering cis-3-(2-chloro-3,3,3-trifluoro-1-propenyl)-2,2-dimethylpropanecarboxylic acid.

11. The process of claim 10 wherein the solvent is removed from the said product mixture prior to acidification, the residue is dissolved in water, acidified, and cooled, and the cis-3-(2-halo-3,3,3-trifluoro-1-propenyl)-2,2,-dimethylcyclopropanecarboxylic acid is recovered by filtration.

12. The process of claim 11 wherein the solvent is a mixture of methanol and water with a volume ratio of methanol to water of about 1.67 and the temperature is reflux temperature.

* * * * *